(12) United States Patent
Ungpiyakul et al.

(10) Patent No.: US 6,404,910 B1
(45) Date of Patent: Jun. 11, 2002

(54) MAKING ABSORBENT ARTICLES USING VISION IMAGING SYSTEM

(75) Inventors: Tanakon Ungpiyakul, Neenah, WI (US); Shawn Timothy Lemery, South Ogden, UT (US); Thomas Arthur Bett; Wayne Allen Bernhardt, both of Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/224,951

(22) Filed: Dec. 31, 1998

(51) Int. Cl.$^7$ .................................................. G06K 9/00
(52) U.S. Cl. ...................................... 382/141; 700/124
(58) Field of Search ........................... 382/141; 348/86, 348/91, 92, 93, 125, 130; 700/95–212; 356/429, 431

(56) References Cited

U.S. PATENT DOCUMENTS

| 4,514,846 A | 4/1985 | Federico et al. ............... 714/45 |
| 4,758,888 A | * 7/1988 | Lapidot ........................ 348/91 |
| 4,837,715 A | 6/1989 | Ungpiyakul et al. .......... 702/82 |

(List continued on next page.)

FOREIGN PATENT DOCUMENTS

| CA | 2044792 | 5/1992 | ............ G05D/5/04 |
| EP | 0 485 691 B1 | 5/1992 | ............ B26D/5/34 |
| JP | 9081233 A | 3/1997 | ............ G05B/23/02 |
| WO | WO 93/07445 | 4/1993 | ............ G01B/21/14 |

OTHER PUBLICATIONS

CheckPoint Machine Vision System, COGNEX, pp. 34–35, 136–138, 143, 146–148, 153–154 & 530, 1995.*
*Acquiring and Displaying Images,* COGNEX, pp. 34–35, 136–138, 143, 146–148, 153–154, and 530., 1995.
"User's Manual Model 1012," *Kodak Ektapro EM Motion Analyzer,* Eastman Kodak Company, 1990. pp. 1.1–7.9.

Primary Examiner—Samir Ahmed

(57) ABSTRACT

Apparatus and method using vision imaging for combined short-term and long-term monitoring and control of a manufacturing operation which produces absorbent articles for absorbing body fluids. The system collects discrete real-time visual images at a rate of at least 50–400 images per minute, up to at least 1200 images per minute, provides an ongoing display of a pattern of such images, and upon occurrence of a triggering event, continues the visual display of the images while sending information representing a limited number set of real-time images to a memory storage system which receives and permanently stores the information, for future retrieval. The data is preferably received in a temporary memory device, and written from there to a second permanent memory device. While the visual images are being sent to the memory storage system, process control logic preferably analyzes the visual images in real time, and sends results signals to manufacturing control, which modifies the manufacturing operation, for example, modifying timing of a process step, shutting the process down, or culling work pieces. A second set of a second limited number of such visual images can be sent to the memory system in response to a second, optionally subsequent, triggering event and/or from a second location. After sending any set of real-time visual images to memory storage, and prior to occurrence of a next triggering event, preferably images are continually collected, received, but few or none of such images are sent to the memory storage device. Image collection is preferably synchronized with advancement of the work pieces or product, or process steps, along the manufacturing process line.

31 Claims, 2 Drawing Sheets

U.S. PATENT DOCUMENTS

| | | |
|---|---|---|
| 5,045,135 A | 9/1991 | Meissner et al. ............. 156/64 |
| 5,138,377 A | 8/1992 | Smith et al. .................. 399/11 |
| 5,195,029 A | 3/1993 | Murai et al. .................. 700/79 |
| 5,200,779 A | 4/1993 | Nawata ........................ 399/24 |
| 5,218,406 A | 6/1993 | Ebner .......................... 399/11 |
| 5,239,547 A | 8/1993 | Tomiyama et al. ......... 714/16.4 |
| 5,251,273 A | 10/1993 | Betts et al. ................... 382/26 |
| 5,286,543 A | 2/1994 | Ungpiyakul et al. .......... 428/74 |
| 5,315,697 A | 5/1994 | Nagamatsu ................. 345/328 |
| 5,333,062 A | 7/1994 | Hara et al. ................. 358/437 |
| 5,359,525 A | 10/1994 | Weyenberg ................ 700/124 |
| 5,365,310 A | 11/1994 | Jenkins et al. ................. 399/8 |
| 5,388,252 A | 2/1995 | Dreste et al. ................. 714/46 |
| 5,388,618 A | 2/1995 | Decock ....................... 139/1 R |
| 5,392,095 A | 2/1995 | Siegel ........................... 399/8 |
| 5,437,278 A | 8/1995 | Wilk ......................... 600/425 |
| 5,452,438 A | 9/1995 | Umeda et al. ................. 714/1 |
| 5,467,355 A | 11/1995 | Umeda et al. ............. 702/184 |
| 5,490,089 A | 2/1996 | Smith et al. .................. 399/81 |
| 5,564,005 A | 10/1996 | Weber et al. ............... 345/326 |
| 5,619,445 A | 4/1997 | Hyatt .......................... 365/45 |
| 5,659,538 A | 8/1997 | Stuebe et al. ............... 700/124 |
| 5,694,528 A | 12/1997 | Hube ........................ 358/1.14 |
| 6,031,567 A * | 2/2000 | Johson ........................ 348/91 |

* cited by examiner

MAKING ABSORBENT ARTICLES USING VISION IMAGING SYSTEM

BACKGROUND OF THE INVENTION

This invention relates to apparatus and methods for monitoring and evaluating manufacturing operations which produce an ongoing stream of discrete absorbent articles effective to absorb body fluids. Such products are typically fabricated as a sequence of work pieces on a continuous web. Such absorbent articles generally comprise an absorbent core confined between a moisture impervious baffle of e.g. polyethylene and a moisture pervious body side liner of e.g. non-woven fibrous material. The absorbent articles are made by advancing one of the webs along a longitudinally extending path, applying the absorbent core to a first one of the webs, and then applying the second web. Other elements such as elastics, leg cuffs, containment flaps, waste bands, and the like are added as desired for the particular product being manufactured, either before or after applying the second web. Such elements may be oriented longitudinally along the path, or transverse to the path, or may be orientation neutral.

Upon the occurrence of certain events, the products fabricated by such manufacturing operations may be moving out of a tolerance range of predetermined required specifications whereupon corrective action should be taken in the manufacturing operation; or the product may fall outside such specifications and should be culled from the product stream.

A variety of possible events in the manufacturing operation can cause the production of absorbent articles which fall outside the specification range. For example, stretchable materials can be stretched less than, or more than, desired. Elements can become misaligned relative to correct registration in the manufacturing operation. Timing between process steps, or speed of advance of an element, can be slightly out-of-tolerance. If such non-catastrophic changes in process conditions can be detected quickly enough, typically process corrections can be made, and the variances from target reduced, without having to shut down the manufacturing operation and without having to cull, and thereby waste, product.

Certain events, however, inherently result in production of out-of-tolerance product whereby no amount of process control can avoid product culling. Exemplary of such events are splices in the base continuous web.

Where product is outside the specification range, and should be culled, it is desired to cull all defective product, but only that product which is in fact defective. If too little product is culled, or if the wrong product is culled, then defective product is inappropriately released into the stream of commerce. If product which in fact meets product specification is culled, the good product is being wasted.

Body fluid absorbing absorbent articles are typically manufactured at speeds of about 50 to about 1200 articles per minute on a given manufacturing line. Accordingly, it is impossible for an operator to hand inspect each and every article so produced. If the operator reacts conservatively, culling product every time he/she has a suspicion, but no solid evidence, that some product may not meet specification, then a significant amount of in fact good product will have been culled. However, if the operator takes action only when a defect has been confirmed using visual inspection, defective product may already have been released into the stream of commerce.

One way for the operator to inspect the product for conformity with the specification range is for the operator to periodically gather and inspect, off-line, physical samples of the product being produced. Random such inspections stand little prospect of detecting temporary out-of-specification conditions. Where such samples are taken in response to a suspected out-of-specification condition, given the high rate of speed at which such articles are manufactured, by the time the operator completes his/her inspection, the suspected offensive condition may have existed long enough that questionable product will have either been shipped or culled without the operator having any solid basis on which to make the ship/cull decision. Further, automated manufacturing process controls may have self-corrected the defect condition before the operator can complete the visual inspection and act on the results of such visual inspection.

While off-line inspection is the primary determinant of quality, and defines the final quality and disposition of the product, on-line inspection, and off-line inspection of on-line-collected data, typically associated with certain manufacturing events, may provide valuable insight into both the operation characteristics of the manufacturing process, and the final quality parameters of the product.

Recent advances in product inspection include use of one or more vision imaging systems having a camera disposed along the path of manufacture. A vision imaging system camera can thus be placed in a fixed location, for collecting visual images of the product at that location. The vision imaging system continuously collects images of the product work pieces as the product precursors pass the point in the manufacturing process which is being monitored. The images so collected are transmitted to a visual display device such as a video monitor at the operator's station, whereby the operator can visually monitor certain visual parameters of the product at the respective location along the manufacturing path.

Such vision imaging systems typically run continuously during manufacturing operations, such that the operator can continuously, or at any time, monitor the condition of the product being manufactured at the given location in the manufacturing line. However, conventional continuous-duty vision imaging systems do not provide any mechanism for the operator to archive any images being viewed.

Some current vision imaging systems can be used to instantaneously capture the full digital representation of a vision image, and to capture and transfer measurement data representing limited portions of each of the images to be evaluated, but have very limited ability to store or transfer full visual images related to that data. The memory storage capacity of such vision imaging systems provides a limited capacity for temporarily or permanently storing vision images so collected. The collected images and data can be transferred to permanent storage within the vision imaging systems, but the imaging system has very limited capacity to permanently store the images, and such permanent storage will compromise the ability to continue collecting data while simultaneously transferring collected data to permanent storage at the production speeds contemplated here of, for example and without limitation, at least 200 inspections per minute.

The capacity to simultaneously collect data, and transfer data to permanent storage, is a function of both the complexity of the inspection of images being captured and analyzed, and the frequency with which images are to be captured. At typical manufacturing speeds for manufacturing absorbent articles such as diapers and incontinence products, namely at least 300–400 units per minute, current vision imaging systems are unable to sustain required rates of ongoing simultaneous capture and transfer of the images available for capture at the rate of one image per unit of production.

Removal or transfer of the data, and restarting of the collection process in such existing vision imaging system typically includes operator intervention, but can be done by pre-programmed computer control. While limited amounts of data can thus be collected and archived from a high speed operation such as illustrated in the drawings, the amount of data which can be collected relating to a given event is quite limited. Typically, current imaging systems will freeze on the first defective image detected. Restarting of the collection process can be pre-programed and thus computer controlled, or can be manual. Accordingly, to the extent the ongoing manufacturing process is producing data that could be useful to the operation and/or analysis of the process, current imaging systems have very limited capability to collect, archive, and then reconstruct vision images of such data. While a limited set of measurement data from such images can be archived, and retrieved, such data is insufficient for reconstructing the desired vision images.

Other vision imaging systems such as KODAK® EKTAPRO® Model 1012 Motion Analyzer can be used to capture full visual images but not to automatically generate measurement data. Such a vision imaging system can collect and display real-time video images, and can store up to 1637 of the most recent frames of video images in memory. The images can be synchronized with the manufacturing operation such that each frame/image shows and represents each successive work piece. However, such a portable systems is unsuited for continuous duty operation, and is unable to retain in storage any but the latest 1637 frames. The stored images can be downloaded to a limited number of models of VCR, but camera recording cannot take place concurrently with the downloading to the VCR. Thus, where a particular set of images is of interest, such images are lost as soon as additional images, greater than the 1637 frames, are taken, or camera recording must be stopped in order to download the images to a VCR. However, as indicated above, the KODAK EKTAPRO system does not, of itself, generate measurement data related to such images without manual intervention.

Accordingly, current systems are unable to automatically and simultaneously capture and transfer both the full digital image and the desired selected measurement data, to permanent storage. Thus, the user is torn between the need to retain certain information which may be valuable for later analysis and the need to continue monitoring the real-time images of the articles being currently produced in the manufacturing operation.

Thus, it is desirable to provide quality control process and/or apparatus capable of both monitoring the real-time condition of the articles being manufactured, and simultaneously capable of selectively archiving certain sets of the visual image data in a memory storage device.

It is further desirable to archive in memory storage only that data which provides an above average probability of containing information of interest for maintaining quality control or for engineering development.

Accordingly, it is desirable to send visual image information to memory storage only upon the occurrence of one or more triggering events related to the manufacturing operation and while camera image recording is continued.

It is desirable that, upon occurrence of the triggering event, the apparatus and/or process automatically sends preselected ones of the images to memory storage as visual image information.

It is desirable that, during the time wherein visual image information is being sent to storage, the visual image display be continued uninterrupted and undisturbed, selecting and displaying images without being affected by the fact that visual images are being transferred to data storage.

It is still further desirable to provide such quality control process and/or apparatus wherein the visual display continues unabated before, during, and after, sending visual images to storage.

It is yet further desirable to provide such quality control process and/or apparatus which first sends the visual image information, to be stored, to a high speed temporary memory storage device at a rate of about 300 to about 1000 visual images per minute, and from the high speed temporary memory storage device, writes the visual image information to a slower speed, but larger capacity permanent memory storage device.

It is further desirable to provide such quality control process and/or apparatus which can continue manufacturing absorbent articles while collecting and displaying a continuous real-time display of the visual images so collected, and which can send at least two sets of visual images to storage at periods spaced in time sufficient to allow the high-speed temporary storage to write the entirety of the first set of images to the permanent storage without interference from the second set.

It is still further desirable to provide such quality control process and/or apparatus including placing identifying information on physical work pieces represented by the visual image information so stored, thus to enable correlation of specific work pieces or absorbent article products with specific visual images so stored.

It is highly desirable to suspend image storage, and to store few if any of such images after completion of any one predefined set of visual images, until occurrence of the next triggering event.

It is still further desirable, in some instances, to collect such visual images at two or more fixed locations along the path of manufacturing operations, in response to triggering events.

It is thus an object of the invention to provide quality control process and/or apparatus capable of both monitoring the real-time condition of the articles being manufactured, and simultaneously capable of selectively archiving certain sets of the visual image data in a memory storage device.

It is another object to archive in memory storage only that data which provides an above average probability of containing information of interest for maintaining quality control or for engineering development.

It is still another object to send image information, preferably as digital data, to memory storage only upon the occurrence of one or more triggering events related to the manufacturing operation and while camera image recording is continued.

It is a further object that, upon occurrence of the triggering event, the apparatus and/or process automatically sends preselected ones of the images to memory storage as visual image information.

It is a yet further object that, during the time wherein visual image information is being sent to storage, the visual image display be continued uninterrupted and undisturbed, selecting and displaying images without being affected by the fact that visual images are being transferred to data storage.

It is a still further object to provide such quality control process and/or apparatus wherein the visual display continues unabated before, during, and after, sending visual images to storage.

It is yet a further object to provide such quality control process and/or apparatus which first sends the visual image information to be stored to a high speed temporary memory storage device at a capacity rate of at least about 300 to about 1000 visual images per minute, and from the high speed temporary memory storage device, writes the visual image information to a slower speed, but larger capacity permanent memory storage device.

It is further an object to provide such quality control process and/or apparatus which can continue manufacturing absorbent articles while collecting and displaying a continuous real-time display of the visual images so collected, and which can send at least two sets of visual images to storage at periods spaced in time sufficient to allow the high-speed temporary storage to write the entirety of the first set of images to the permanent storage without interference from the second set.

It is still a further object to provide such quality control process and/or apparatus including placing identifying information on digital images of specified work pieces, thus to enable correlation of specific work pieces or absorbent article products.

It is yet another object to suspend image storage, and to store few if any of such images after completion of any one predefined set of visual images, until occurrence of the next triggering event.

A still further object is to collect such visual images at two or more fixed locations along the path of manufacturing operations, in response to triggering events.

SUMMARY OF THE DISCLOSURE

Some of the objects are achieved in a first family of embodiments of the invention comprehending a method of using a vision imaging system in a manufacturing operation wherein the manufacturing operation produces an ongoing stream of discrete absorbent article work pieces and products made therefrom, effective to absorb body fluids. The method produces such absorbent articles on a continuous web, and comprises operating a vision imaging system which collects visual images at one or more generally fixed locations in the manufacturing operation, typically collecting discrete visual images at a rate of at least 50 images per minute, preferably but without limitation up to about 1200 images per minute, at each fixed location, preferably at least about 200 up to about 1000 images per minute, more preferably at least about 300 images per minute, still more preferably at least about 400 up to about 900 images per minute, and most preferably about 600 up to about 800 images per minute. The method further provides an ongoing visual image display of a pattern of successive such images so collected, each such visual image representing a successive at least one of a workpiece or a product, or a process condition, associated with the manufacturing operation. The method further comprises selecting one or more triggering events, planned or unplanned, related to the manufacturing operation, and upon occurrence of any one of the triggering events, continuing the ongoing visual display of the pattern of images, typically at substantially the same image collection rate, while concurrently sending data representing a limited number set of such real-time visual images so collected, to a memory storage device. Such memory device should be a high-speed memory device such as a digital memory device, for example a relatively high-capacity random-access memory device or a buffer memory device.

The image collection rate can be adjusted as needed at any time, including while image data is being transferred from temporary storage to permanent storage.

The method preferably includes sending to the memory storage device at least some of the same visual images as are displayed on the image display device.

The method preferably includes, upon conclusion of the sending of the set of images to the digital memory device, continuing the ongoing collection of visual images and thereby continuing to provide an ongoing real-time visual image display of the pattern of images representing at least one of the work piece or product, or the process.

In preferred embodiments, the method includes writing the visual image data from the memory storage device to a second, slower speed, higher capacity, memory storage device.

The method preferably includes synchronizing the collection of images such that each subsequent image so collected shows a full length and a full width of one such workpiece or product, or one such process condition, per frame and one visual frame per workpiece or product, or process condition. Preferably, sequential images represent sequential work pieces or products, or sequential process conditions.

Preferred such methods include, while sending the set of visual images to the storage device, using computer logic to analyze, in real time, the visual images so collected, and sending corresponding results signals to control apparatus controlling the manufacturing operation, and the control apparatus processing the results signals and, based on the processing of such results signals, issuing control commands to thereby modify the manufacturing operation. Such control command can, for example, modify timing of a process step, or result in culling work pieces from the manufacturing operation.

In some embodiments, the control command stops the manufacturing operation. In such embodiments, when the required condition is detected on the manufacturing line, process control logic issues a command to generate e.g. a stop signal. The stop signal activates a sequence in the software that enables the process to shutdown e.g. through electronic and/or mechanical braking means or withdrawal of driving power. The required condition can be triggered via automated sensor or operation intervention. In some embodiments, the control command provides an alarm to an operator.

The method can optionally include continuing to run the manufacturing operation upon conclusion of the sending of the set of visual images to the memory storage device, and while so continuing to run the manufacturing operation, sending a second set of a second limited number of real-time visual images, which number may or may not be the same as the number of images in the first set, to the e.g. digital memory storage device in response to a second triggering event.

The method can include incorporating identifying information with the stored full digital image information representing the work pieces, thus to enable correlation of specific images so stored with specific work pieces.

The method preferably includes, after completion of the sending of the set of real-time visual images and prior to occurrence of a second triggering event, sending to the digital memory storage device few or none of the real-time visual images being collected.

Preferred embodiments of the method preferably comprehend storing the images in digital format, including maintaining substantially full digital integrity of the visual images so stored, compared with the images as collected, thereby to enable substantially full visual reproduction of the visual images so stored.

In some embodiments, the recited fixed location comprises a first fixed location, the set of visual images comprises a first set of visual images, and the method includes collecting visual images at a second generally fixed location in the manufacturing operation, in response to a triggering event, and sending a limited-number second set of real-time visual images so collected to the digital memory, and optionally including segregating the first and second sets of visual images from each other in the memory storage device.

The triggering event which triggers sending the second set of images to memory may be the same triggering event that triggers sending the first set of images to memory. Sending the second set of images to memory storage may occur concurrently with sending the first set of images to memory storage, in part concurrently, or subsequent to completion of sending the first set of images to memory storage.

The invention further comprehends apparatus for capturing, and concurrently displaying and storing in memory, visual images of a process which manufactures absorbent articles effective to absorb body fluids. The apparatus comprises manufacturing machines manufacturing such absorbent articles, the machines including control apparatus effective to control operations of the manufacturing machines so as to fabricate such absorbent articles according to predetermined parameters; a vision imaging system collecting real-time discrete visual images at a generally fixed location in association with the manufacturing machines, of a work piece or a product, or a process condition, associated with the absorbent articles being produced, and presenting a real-time visual image display of the images so collected, on an image display device, and sending corresponding results signals to the control apparatus, thereby to control the manufacturing machines; and a memory storage system receiving a limited-number set of the real-time visual images, substantially less than the entirety of all the visual images so collected and displayed by the vision imaging system.

In preferred apparatus, the memory storage system comprises a high-speed temporary memory storage device, and a permanent memory storage device receiving the stored images from the temporary memory storage device.

The memory storage system preferably receives the set of visual images concurrent with the display of real-time images on the display device. Preferably, at least some of the visual images received in the memory storage system are the same images as are being concurrently displayed on the image display device.

Figure 1:
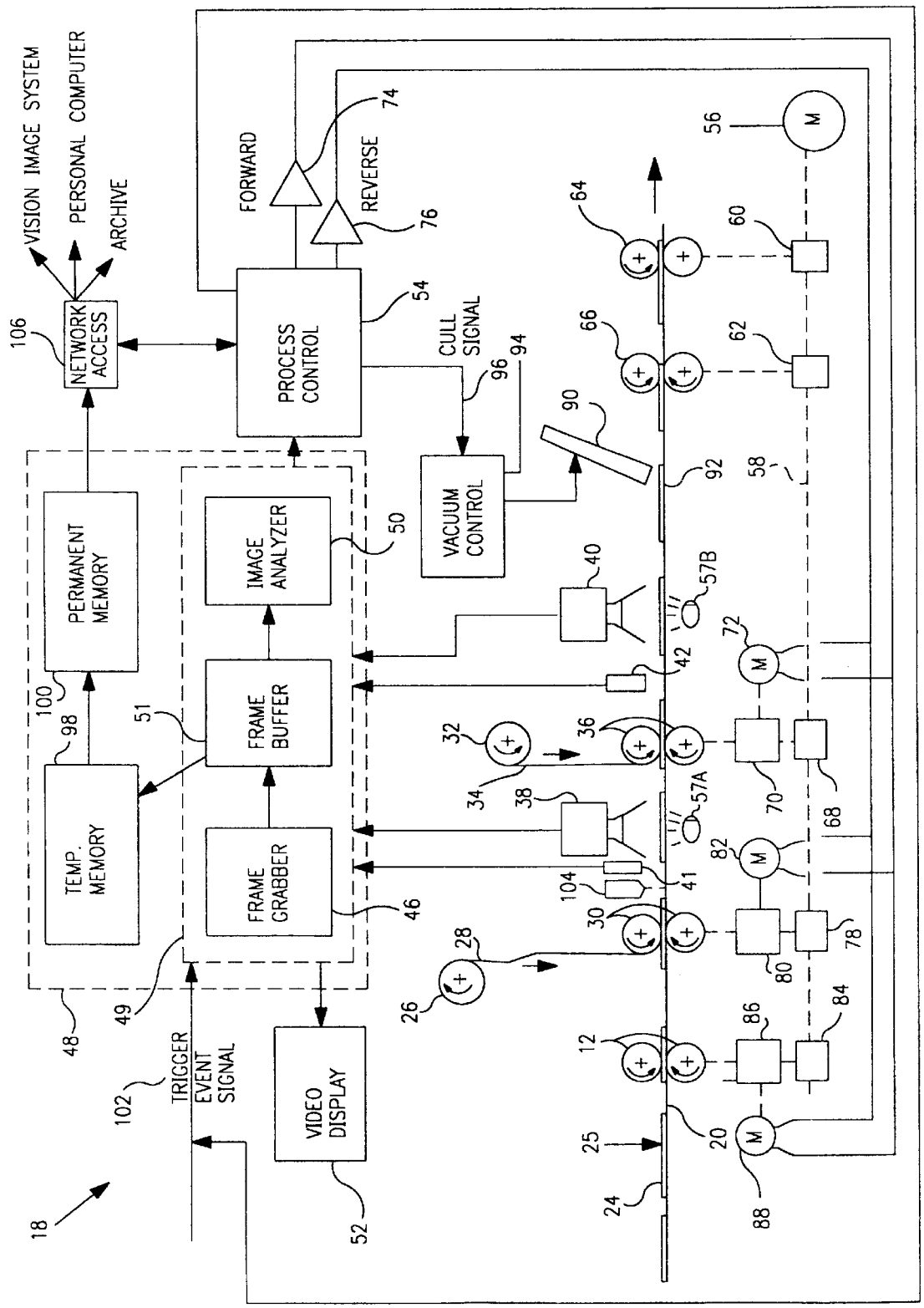
FIG. 1 is a side elevation view of absorbent article manufacturing apparatus of the invention, including a control system comprising a vision imaging subsystem comprising image collection, display, and storage apparatus and controls, as well as interface of the vision imaging system with the manufacturing process control system and a memory storage system.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

Figure 2:
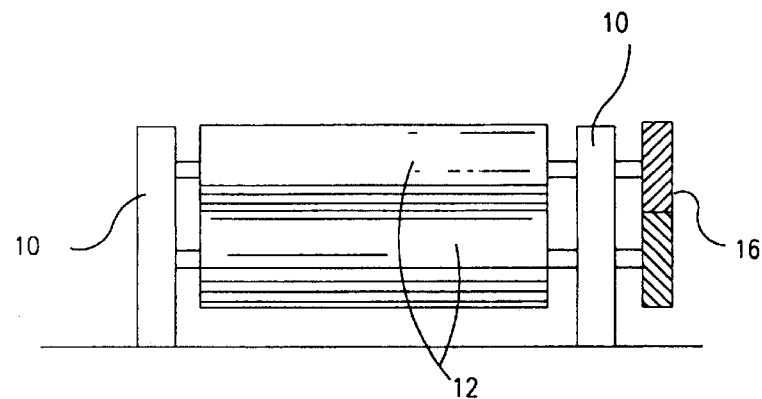
FIG. 2 is a representative end elevation view, also substantially schematic, of a line of manufacturing machines of FIG. 1, used to make absorbent articles.

With reference to the drawings, and more particularly to FIG. 2, the numeral 10 designates a pair of side frame elements which define a longitudinally extending processing path for the processing of absorbent articles according to the invention. Rotatably mounted on side frames 10 are a pair of processing rolls 12 driven by gears 16. Processing draw rolls 12 can be seen toward the left portion of FIG. 1.

Now referring to FIG. 1, the absorbent article producing apparatus of the invention is illustrated schematically at 18. Beginning at the left end of FIG. 1, an underlying web 20, for example a moisture impervious baffle web, is shown being advanced toward the right along the longitudinally extending path, by draw rolls 12. Omitted for clarity of presentation is the upper confining web such as a body side liner web.

Absorbent pads 24 are shown disposed on web 20 at spaced intervals generally corresponding to the respective separate and distinct work pieces 25 or products being fabricated into absorbent articles along the processing path. Additional elements such as leg cuffs, containment flaps, waist bands, and the like are placed, positioned, and otherwise consolidated onto or into continuous web 20, or onto or into each other, at various work stations along the processing path, in the process of fabricating the absorbent articles.

For example, unwind 26 supplies leg cuff material 28 which is placed on web 20 at rolls 30. Similarly, unwind 32 supplies waist band material 34 which is placed on web 20 at rolls 36.

Camera 38 is positioned between the work station defined by rolls 30 and the work station defined by rolls 36. Optional camera 40 is positioned downstream of rolls 36. Image trigger device 41 is between rolls 30 and camera 38. Image trigger device 42 is between rolls 36 and camera 40. Image trigger devices 41 and 42 are activated by sensing, for example, the passing of a specific element on each work piece, for example an outwardly-extending ear 44, illustrated in FIG. 3. This activation provides a signal to vision system 49 of imaging system 48. Imaging system 48 includes vision system 49, temporary memory 98, and permanent memory 100. Vision system 49 includes frame grabber 46, frame buffers 51, and image analyzer 50.

The image trigger sends detect signals to frame grabber 46 and strobe light 57A or 57B. The detect signal thus synchronizes firing of the respective strobe light and grabbing of the respective frame or image of the respective product by frame grabber 46, being transmitted from the respective camera. The grabbed frame is transmitted by frame grabber 46 to frame buffer 51 in registration with movement of the respective work pieces on the manufacturing line such that the frame grabber transfers a visual image of each work piece in accord with detect signals created by the passing of respective work pieces past image trigger devices 41 and 42. While image trigger devices 41 and 42 are illustrated between the rolls and the respective cameras, the trigger devices could be at any location on the processing line compatible with timely collection of frames being recorded by the respective camera or cameras.

The visual images are sent by frame grabber 46 to frame buffers 51, thence to image analyzer 50 and, upon request by trigger event signal 102, to temporary memory 98. After being processed by vision system 49, the processed camera signal is sent to video image display device 52. The frame grabber, the frame buffer, the image analyzer, the temporary memory, and the permanent memory are all elements of imaging system 48 in the illustrated embodiment.

Figure 3:
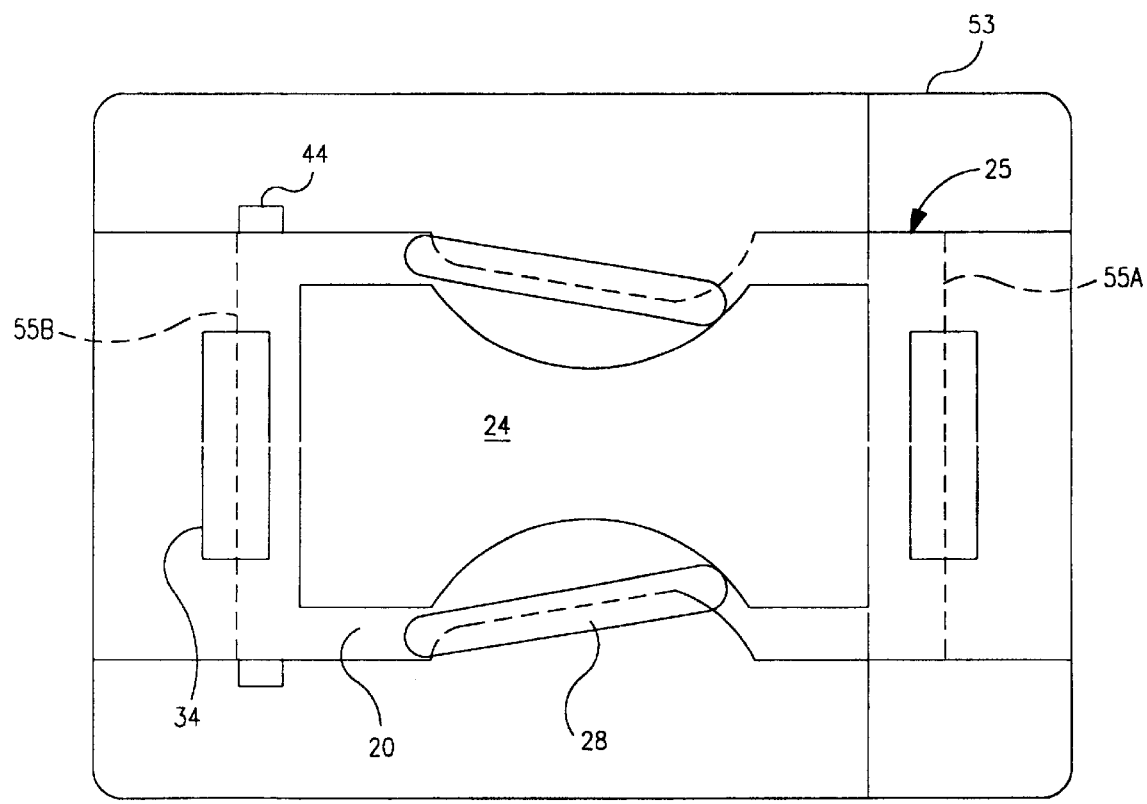
FIG. 3 is a plan view illustrating a typical visual image displayed to the operator and stored in memory, and showing a portion of the absorbent article manufacturing operation.

Referring to FIG. 3, the closed outline 53 represents the camera field of view and it will be seen that outline 53 embraces somewhat more than the length of a single work piece 25, but less than the length of two work pieces, disposed generally in the center of outline 53, between projected transverse lines of severance 55A, 55B, which define the boundaries between sequential work pieces.

A suitable imaging system for use in the invention, including camera, video image display device, frame grabber, and image analyzer, is available from Cognex Corporation, Natick, Mass.; USA, as CHECKPOINT 800. Suitable software for collecting displaying, and analyzing the visual images so collected, of individual ones of the absorbent articles being fabricated in the manufacturing operation, is also available from Cognex Corporation.

The visual image signals collected by camera 38 and optional camera 40 are processed by frame grabber 46 and image analyzer 50, thereby converting the images received from the camera or cameras into digitized representations of the visual images so recorded. The results of such analysis are fed to process control 54. Process control 54 receives such results signals and issues output commands, as appropriate, to adjust and modify the manufacturing process in order to rectify any anomalous readings and to steer the manufacturing operation toward pre-selected target specifications stored in the process control memory.

Thus, signals may be sent to speed up, or slow down, the absolute speed, or to advance or retard the timing, of one or more of the process steps at respective work stations in the processing line. Further, signals may be sent to cull product from the processing line.

Referring again to FIG. 1, the number 56 designates the main drive motor which powers the machinery operating the absorbent article production line, which main drive motor is employed to turn a line shaft 58 coupled by gear boxes 60, 62, to draw rolls or turning rolls 64, 66 respectively.

Line shaft 58 is also coupled by gear box 68 to differential 70 which is operated by motor 72 in response to signals from process control 54 through a forward signaling device 74 or a reverse signaling device 76, both of which are coupled to motor 72, to advance or retard the speed of draw of rolls 36, and thereby to advance or retard the speed of flow of work pieces through rolls 36, and accordingly, the frequency at which waist band material 34 is applied to the work pieces.

Similarly, line shaft 58 is coupled by gear box 78 to differential 80 which is operated by motor 82 in response to signals from process control 54 through signaling devices 74, 76, both of which are also coupled to motor 82, to advance or retard the speed of flow of work pieces through rolls 30, and accordingly, the frequency at which leg cuff material 28 is applied to the work pieces.

Further, line shaft 58 is coupled by gear box 84, which contains gears 16, to differential 86 which is operated by motor 88 in response to signals from process control 54 through signaling devices 74, 76, both of which are also coupled to motor 88, to advance or retard the speed of draw of work pieces 25 into rolls 12, and accordingly, the speed at which web 20 and the elements resident thereon are fed toward the respective downstream work stations. After an image has been analyzed by analyzer 50 and has been processed by process control 54, correction logic embodying the range of specifications acceptable for the work piece can be delivered to signalizing devices 74 (forward) and/or 76 (reverse), or to vacuum control 94 for culling work pieces.

Additional work stations, not shown, can be employed in similar manner to place and/or affix others of the elements of the absorbent articles, directly or indirectly, onto web 20.

Vacuum shoe 90 is positioned over work station 92 downstream of camera 40, and is controlled by vacuum control 94. In circumstances wherein the signals received by process control 54 indicated that the work piece which was imaged and analyzed is out of tolerance, process control 54 sends a cull signal 96 to vacuum control 94, activating vacuum to vacuum shoe 90 at the appropriate time to cull the individual work piece which gave the out-of-tolerance information. Where desired, and where suitable lead time is available to the cull system, vacuum control 94 can be programmed to cull, in addition, a specified number of work pieces before and/or after the work piece which yielded the out-of-tolerance visual image information.

In addition to providing an output to process control 54, vision system 49 also outputs visual image information to high speed temporary memory 98 which subsequently outputs the visual image information to permanent memory 100. The visual image information inputted from vision system 49 to temporary memory 98, and subsequently to permanent memory 100, is sufficient in quantity and satisfactory in quality and specificity, to generally re-create the individual vision images collected by camera 38 and/or camera 40. Thus, the stored information maintains substantially the full integrity, typically full digital integrity, of the visual images so stored, as compared to the images recorded or collected by camera 38 or 40. Accordingly, the visual images so stored enable the user to substantially reproduce the respective images which were available to the operator in real-time during manufacturing of the respective absorbent articles.

A temporary memory suitable for general purpose use in association with the invention is a VME memory card having memory capacity of up to about 1 Gigabyte, and is available from Chrislin Industries Inc., Westlake Village, Calif., USA. Such temporary memory can capture, and store in memory, visual images of typical absorbent articles such as those described herein, at the high capture/store rate of at least about 500 images per minute, up to about 1000 images per minute.

Communication between vision system 49 and temporary memory device 98 requires use of a suitable protocol such as a VME standard to transfer data across the computer backplane to a temporary memory device. Such a temporary memory is a VMEbus standard IEEE 1014.

While the high image capture rate of temporary memory 100 is critical to the invention, such high capture rate memory storage devices have certain limitations. First, such devices are costly in terms of the cost per image so captured and stored. Further, high capture rate devices such as the buffer memory devices described above are temporary memory storage devices within the context that such storage devices retain captured information in memory only so long as the respective memory device is powered. and lose all information stored in memory when power is removed from such memory devices.

Accordingly, it is critical that the visual image information received in the high-speed temporary memory storage, e.g. buffer, device be transferred to a permanent memory storage device. A typical suitable permanent memory storage device is, for example, a hard drive such as hard drives commonly used in personal computers. Where a larger amount of memory is desired than is available on a conventionally-available hard drive, a combination of such hard drives can be coupled together in well known manner to thereby provide the composite capacity of all the hard drives so coupled together.

The value of temporary memory device 98 is to enable real-time transfer of the visual image information from the imaging system. Conventional permanent memory devices are too slow for such real-time transfer at any reasonable interface cost, whereby the temporary memory device is used.

The value of permanent memory 100 is three-fold. First, once the information has been received into permanent memory, such permanent memory can be accessed by a variety of users, if desired, through a typical networked computer interface system. Second, permanent memory retains the information in memory when power is turned off and wherein power is disconnected from the permanent memory storage device, and lost. Thus, once the visual image information is disposed in permanent memory, the risk of loss from removal or interruption of power is obviated. Third, permanent memory is less costly than temporary e.g. buffer memory.

Accordingly, images which conventionally have been available only to the operator on the manufacturing line, and which have been available only as real-time images, are, by virtue of the invention, now available at any time, to anyone having access to the permanent memory device, such as from a remote computer terminal remote from network access 106. Similarly, the data stored in process control 54 can be polled and accessed from a remote terminal, through network access 106, thus allowing direct correlation and comparison of specific images with specific process control information. Thus, in the invention, the images remain available for real-time use at the manufacturing line, as before; and can, in addition, be accessed either on or off the manufacturing floor at a later date by any authorized user, for further analysis at whatever level of analysis is desired.

Thus, for the first time, visual images of the product, or the process, can be permanently archived, and associated with specific manufacturing periods of specific manufacturing events, without interrupting ongoing collection of such visual images. In addition, the visual images so stored in memory can be re-created from the stored data in the same or another vision system, or can be stored and re-used in other software applications such as in combination with bit-map systems. However stored, and retrieved, such retrieved information can then be used for in-depth analysis of the results, on the work pieces, of specific events occurring on the manufacturing line.

Individual images recorded or received at cameras 38, 40, and ultimately stored in permanent memory 100, can be accessed individually at will from permanent memory 100, and analyzed as desired, any time after collection. For example, an analyst can choose to review and analyze a certain set of images based on the occurrence of a triggering event, or a set of images recorded according to the time at which the images were collected.

As is well known for use of such computer memory devices, visual image data which is permanently stored in e.g. permanent storage device 100 can be erased at will in order to make such storage space available for use to store other information.

The above described imaging system 48 has a rate capacity of producing a visual image of each and every work piece produced by the manufacturing operation. Indeed, it is desirable to the line operator that the imaging system does produce a visual image of each and every work piece.

However, it is not desirable to store a visual image of each and every work piece. Such storage of all visual images so produced would require an inordinate amount of memory storage capacity. In addition, since the rate of production of such images is greater than the input rate capacity of a typical hard drive permanent memory storage device to receive such information, such storage would have to be carried out in parallel with multiple permanent memory devices concurrently receiving memory storage inputs. Still further, the amount of data so stored in memory would make it difficult for an inquirer to identify images of particular interest for further study and/or to correlate any such images with specific events in the manufacturing process.

Accordingly, it is an important feature of this invention that visual images be transferred from image analyzer 50 to a memory storage device such as temporary buffer memory 98 only upon the occurrence of selected, preferably predetermined, triggering events. By limiting transfers to memory to only those images associated with certain triggering events, the amount of storage media required is appropriately limited, and the amount of data stored, and which may be reviewed to find evidence of an event of interest, is also limited.

The suggested Cognex Imaging system can be programmed to transfer to memory a specified number of visual images upon the occurrence of a triggering event. The transfer can begin so as to take samples wherein the work piece being imaged when the triggering occurred is at or toward the beginning of the sample, in the midst of the sample, or at or toward the end of the sample.

The user can specify any event of interest as a triggering event for collection of visual image data. For example, a splice in any of the feed webs 20, 28, 34 might be specified as a triggering event. A certain amount of change in line speed might be specified as a triggering event. A certain amount of change in tension of one or more webs might be specified as a triggering event. An out of tolerance condition might be specified as a triggering event. Additionally, a manual trigger can be used to initiate image capture, as can a timer, or a random number generator.

However the triggering event is created, manufacturing controls are configured such that, upon the occurrence of a triggering event, a signal 102 is generated, e.g. by a sensor or by a process control command, and transmitted to vision system 49, triggering frame buffer 51 to begin sending visual images to memory, and specifying how many images are to be sent to memory, or for how long a period of time images are to be sent to memory.

Thus, upon the occurrence of a triggering event, a defined set of a limited number of real-time visual images so collected by frame grabber 46 is sent to vision system 49, thence to temporary memory device 98. Preferably while information is still being received by memory device 98, temporary memory device 98 begins transferring the visual image information to permanent memory device 100 at the slower rate at which the permanent memory device is capable of receiving and storing such information.

Accordingly, in preferred embodiments, part of the visual image information has already been transferred to permanent storage device 100 by the time the last of the set of images has been received in high speed memory 98. Accordingly, memory device 98 acts as an accumulator to temporarily take up the excess volume of visual images being transferred from vision system 49, until memory device 100 can receive the balance of the set of images.

Should a second triggering event occur before the last ones of the first set of images has been transferred to memory device 100, temporary memory device 98 receives the second set of images, and transfers such second set of images to memory device 100 after completing transfer of the first set of images. In some embodiments, such first and second sets of visual images are segregated from each other, as separate and distinct sets of image information, in at least one of the respective memory storage devices.

Upon completion of transfer of a given set of visual images according to a triggering event, preferably no more visual images are transferred to memory devices 98, 100 until the next triggering event occurs. While a few visual images may be transferred to storage memory for historical record-keeping purposes, e.g. to keep an historical record of product made and/or shipped, the frequency at which such images will be stored is significantly less, namely less than 10%, preferably less than 2%, as frequent as the frequency with which images are stored upon the occurrence of a triggering event.

A typical set of images includes images of about 1 to about 1000 consecutive work pieces in the processing line. A range of about 1 to about 200 work pieces is contemplated for typical use in the invention. Storing fewer than the low number of work pieces mentioned may miss the evidence of the triggering event. Storing greater than the high number of work pieces mentioned will inordinately increase storage costs, albeit computer memory, and may create a database so large that finding useful information may be quite difficult, or at least inefficient.

The illustrated embodiments indicate use of one or two cameras 38, 40. Typically, use of one camera is adequate to indicate the strengths or weaknesses of the manufacturing operation. However, where an anomaly exits, or is difficult to correct, additional cameras, such as camera 40, may be set up at corresponding additional locations along the manufacturing line, and connected into the imaging system 48, and the memory system (device 98 and device 100), in order to collect and permanently store additional information directed toward discovering the source of the anomaly. Accordingly, the imaging system can produce and store in memory a second set of data, either before, e.g. shortly before, during, or after, e.g. shortly after, collecting and storing a first set of data. The second set of data can be obtained from the same camera, e.g. directed at the same location on the processing line, as the first set of data, or can be obtained from a second camera pointed at the same location on the processing line or can be located at a different work station, recording a different step in the process.

By associating suitable identification indicia with each transfer of a set of visual images to storage, the reviewing artisan can search first for the identification indicia, and having found the identification indicia, and can then focus on the parameters of interest associated with the respective visual images.

Where it is desired to correlate specific physical samples to the visual images of such samples, an article-specific code, different for each work piece so coded, can be printed on the respective work pieces 25, as at, for example, ear 44. Such code can be printed by e.g. a non-contact, e.g. ink-jet, printer 104 located up-stream of the respective camera. In the alternative, a common code, specific to the triggering event, can be printed on each work piece associated with the triggering event.

While not critical to the invention, it is preferred that the visual images sent to memory devices 98, 100 to be the same images sent to display device 52. In such instance, the images available for review later are the same images viewed by the operator in real time.

The invention has been described above generally in terms of known or planned triggering events. However, imaging system 48 can be programmed to trigger storage of visual images in memory upon the occurrence of a wide variety of unplanned events, for example, any occurrence of any out-of-tolerance event, or any unplanned event.

In some embodiments, the video camera or cameras take visual images of fewer than all of the work pieces being processed in the manufacturing operation. Where desired, a camera can be programmed to collect images of every second work piece, every third work piece, or any other desired fraction of the work pieces. Such selection can collect images at regular intervals, or at selected intermittent intervals. For example, a camera control might be programmed to command taking images of a certain set/number of sequential work pieces, for example 3 work pieces, then skip the next set of work pieces, for example 5 work pieces. The actual interval between work pieces whose image is recorded, and the pattern of which work pieces images are to be collected, is a matter of selection for the artisan setting up the image collection.

As used herein, "absorbent article" refers to a class of products worn on the human body, and used generally for promotion of human hygiene by the absorption of body fluids and other exudates. Examples of such absorbent articles include, without limitation, diapers, training pants, incontinence pads, feminine hygiene pads, interlabial pads, and the like.

As used herein, a "high speed" memory storage device is a storage device capable of receiving at least about 50, preferably at least about 200, and more preferably at least about 300, still more preferably at least 400 or 500, up to at least about 1200, visual images per minute from cameras of the nature described herein for use in the invention, and must be able to track the unit rate of production of products of interest to the imaging system. Commonly available such memory devices are variously known as Random Access Memory devices, and/or Buffer Memory devices, both being well known in the art. Typically available such memory storage devices retain the data only so long as power is maintained on such devices, and wherein any data stored therein is lost when electrical power is terminated. Accordingly, such memory devices are not suitable for permanent storage of data. Rather, in the invention the data is written from the high speed temporary storage device to a lower speed, permanent memory storage device.

The number of images collected per minute is controlled by signals, from the processing line, indicating the frequency of passage along the processing line, of work pieces whose images are to be collected.

As used herein, a "lower speed" memory storage device is any memory storage device which is unable to receive visual images of absorbent article-type products from frame buffers 51 of the nature desired herein for use in the invention, usually at a rate of less than about 500 visual images per minute. Typical such memory devices are hard drives such as are commonly employed in personal computers. Such hard drives are available in a variety of sizes, and in a range of input speeds, wherein large amounts of image data can be readily stored in permanent memory, at reasonable cost per image.

The number of images which can be transferred over a given unit of time is a function of the complexity of the image inspections, and the resolution of the images. The more complex the image inspection and/or the higher the image resolution, the slower the transfer rate capacity of the vision system 49.

As used herein, reference to a "generally fixed" location where visual images are collected means that the image collection element such as a camera is fixedly mounted to a physical support, and is directed to a specific step or steps in the manufacturing operation. Thus, "generally fixed" refers to a camera fixed in location but with capability to digitally or optically zoom the image to facilitate inspection of certain elements of the workpiece or workpieces, while not moving the camera from its mounted location. The cameras can, of course, be moved and subsequently recalibrated.

Preferably, the camera is fixed in both location and direction of aim, such that sequentially collected images represent common location and common direction of aim, of the camera.

As used herein, "pattern of images" refers to an ongoing selection of images according to a selection pattern. The selection pattern can select, and therefore collect, an image specific to each work piece, product, or process condition. The selection pattern can, in the alternative, select and collect an image according to an alternative pattern, for example collecting an image of every second or every third work piece, product, or process condition, or collecting an image of every work piece, product, or process condition for a limited number of images, at regularly-spaced intervals. The above-described patterns are exemplary only, and not limiting, as other patterns are now obvious and viable in the invention.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, What is claimed is:

1. A method of using an imaging system in a manufacturing operation wherein the manufacturing operation produces an ongoing stream of discrete absorbent article work pieces and products made therefrom, effective to absorb body fluids, the method producing such absorbent articles from a continuous web, and comprising:
  (a) operating an imaging system collecting visual images in the manufacturing operation and thereby collecting discrete real-time visual images showing full lengths and full widths of respective ones of the work pieces, at a rate of at least 50 images per minute, and providing an ongoing visual image display of a pattern of such images representing at least one of a work piece or a product, or a process condition, associated with the manufacturing operation;
  (b) selecting one or more triggering events, planned or unplanned, related to the manufacturing operation;
  (c) upon occurrence of any one of the triggering events, continuing the ongoing visual display of successive images of successive work pieces being processed while automatically concurrently sending data representing a limited number set of full length and full width such real-time visual images so collected, to a memory storage device; and
  (d) after a respective said work piece, or product, or respective process condition, which caused the occurrence of the triggering event, has left the manufacturing operation, analyzing the data representing the limited number of images so collected.

2. A method as in claim 1, including sending the memory storage device at least some of the same visual images as are displayed on the image display device.

3. A method as in claim 1 including, upon conclusion of the sending of the set of images to the digital memory device, continuing the ongoing collection of visual images as in step (a) and thereby continuing to provide an ongoing real-time visual image display of the pattern of images representing at least one of the work piece or product, or the process.

4. A method of claim 1, including writing the visual image data from the memory storage device to a second, slower speed, higher capacity, memory storage device.

5. A method as in claim 1, including sending the discrete visual images to the memory storage device at a rate of at least 200 images per minute.

6. A method as in claim 1, including sending the discrete visual images to the memory storage device at a rate of at least 300 images per minute.

7. A method as in claim 1, including sending the discrete visual images to the memory storage device at a rate of at least 400 images per minute.

8. A method as in claim 1, including synchronizing the collection of images such that each sequential image shows a full length and a full width of one such work piece or product, or one such process condition, and one visual image per work piece or product, or process condition.

9. A method as in claim 7 wherein successive images represent successive work pieces or products, or sequential process conditions.

10. A method as in claim 1 including, while sending such set of visual images, the visual images having full digital integrity, to the storage device, using computer logic to analyze, in real time, the visual images so collected, and sending corresponding results signals to control apparatus controlling the manufacturing operation.

11. A method as in claim 10, including the manufacturing control apparatus processing the results signals and, based on the processing of such results signals, issuing a control command to thereby modify the manufacturing operation.

12. A method as in claim 11 wherein the control command modifies timing of a process step.

13. A method as in claim 11 wherein the control command stops the manufacturing operation.

14. A method as in claim 11 wherein the control command provides an alarm to an operator.

15. A method as in claim 11 wherein the control command results in culling work pieces from the manufacturing operation.

16. A method as in claim 1, including continuing to run the manufacturing operation upon conclusion of the sending of the set of visual images to the memory storage device, and while so continuing to run the manufacturing operation, sending a second set of a limited number of real-time visual images to the memory storage device in response to a second triggering event.

17. A method as in claim 1, including incorporating identifying information, with the stored image information representing the work pieces, thus to enable correlation of specific visual images so stored visual with specific work pieces.

18. A method as in claim 1, the method including, after completion of the sending of the set of real-time visual images and prior to occurrence of a second triggering event, sending to the memory storage device few of none of the real-time visual images being collected.

19. A method as in claim 1, including maintaining substantially full digital integrity of the visual images so stored, compared with the images as collected, thereby to enable substantially full visual reproduction of the visual images so stored.

20. A method as in claim 1, the method including collecting said visual images, using said imaging system, from a first generally fixed location in said manufacturing operation, the set of visual images comprising a first set of visual images collected from the first generally fixed location, and including collecting visual images at a second generally fixed location in the manufacturing operation, in response to a triggering event, and sending a limited-number second set of real-time visual images so collected from the second generally fixed location to a digital memory.

21. A method as in claim 20, including segregating the first and second sets of visual images from each other in the memory storage device.

22. A method as in claim 1 wherein said memory storage device is a digital memory storage device.

23. A method as in claim 22 wherein the digital memory storage device is a temporary memory storage device, and including transferring the visual images from the temporary memory storage device to a permanent memory storage device.

24. A method of using an imaging system in a manufacturing operation wherein the manufacturing operation produces an ongoing stream of discrete absorbent article work pieces and products made therefrom, effective to absorb body fluids, from a continuous web, the method comprising:

(a) operating an imaging system, including a vision system, and thereby collecting visual images in the manufacturing operation and thereby collecting discrete visual images at a rate of at least 50 images per minute, and providing an ongoing visual image display of a pattern of such images representing at least one of a work piece or a product, or a process condition, associated with the manufacturing operation;

(b) selecting one or more triggering events, planned or unplanned, related to the manufacturing operation; and (c) upon occurrence of any one of the triggering events, continuing the ongoing visual display of the pattern of images while concurrently sending data representing a limited number set of real-time visual images so collected, to a high-speed temporary memory storage device outside the vision system, and including transferring the visual images from the temporary memory storage device to a lower-speed but permanent memory storage device.

25. Apparatus for capturing, and concurrently displaying and storing in memory, visual images of a process which manufactures absorbent articles effective to absorb body fluids, said apparatus comprising:

(a) manufacturing machines manufacturing such absorbent articles;

(b) control apparatus effective to control operations of the manufacturing machines so as to fabricate such absorbent articles according to a range of predetermined parameters;

(c) an imaging system, including a vision system, and thereby collecting real-time discrete visual images, at a generally fixed location in association with said manufacturing machines, of a work piece or a product, or a process condition, associated with the absorbent articles being produced, and providing data representing such visual images to a real-time image display device, and sending corresponding results signals to said control apparatus, thereby to control said manufacturing machines; and (d) a memory storage system, outside said vision system, receiving a limited-number set of the real-time visual images, substantially less than the entirety of all the visual images so collected and displayed by said vision system.

26. Apparatus as in claim 25, said memory storage system comprising a high-speed temporary memory storage device, and a permanent memory storage device receiving the stored images from said temporary memory storage device.

27. Apparatus as in claim 25, said memory storage system receiving the set of visual images concurrent with the display of real-time visual images on said image display device.

28. Apparatus as in claim 25, said memory storage system receiving, as the set of visual images, at least some of the same visual images as are displayed on said image display device.

29. Apparatus as in claim 26, said memory storage device receiving the discrete visual images at a rate of at least 200 images per minute.

30. Apparatus as in claim 26, said memory storage device receiving the discrete visual images at a rate of at least 300 images per minute.

31. Apparatus as in claim 26, said memory storage device receiving the discrete visual images at a rate of at least 400 images per minute.

* * * * *